(12) United States Patent
Arata

(10) Patent No.: US 7,732,486 B2
(45) Date of Patent: Jun. 8, 2010

(54) ANHYDROUS SILVER DIHYDROGEN CITRATE COMPOSITIONS

(75) Inventor: Andrew B. Arata, Lake City, FL (US)

(73) Assignee: Pure Bioscience, El Cajon, CA (US)

( * ) Notice: Subject to any disclaimer, the term of this patent is extended or adjusted under 35 U.S.C. 154(b) by 0 days.

(21) Appl. No.: 11/729,175

(22) Filed: Mar. 27, 2007

(65) Prior Publication Data

US 2007/0185350 A1    Aug. 9, 2007

Related U.S. Application Data

(63) Continuation of application No. 11/298,130, filed on Dec. 8, 2005, now abandoned, which is a continuation of application No. 10/928,638, filed on Aug. 27, 2004, now abandoned.

(60) Provisional application No. 60/498,347, filed on Aug. 28, 2003.

(51) Int. Cl.
*A01N 55/06* (2006.01)
(52) U.S. Cl. ............................................. 514/497
(58) Field of Classification Search .................. None
See application file for complete search history.

(56) References Cited

U.S. PATENT DOCUMENTS

| | | |
|---|---|---|
| 2,658,072 A | 11/1953 | Kosmin |
| 3,303,090 A | 2/1967 | Huffman et al. |
| 3,422,183 A | 1/1969 | Ellison |
| 3,600,186 A | 8/1971 | Mattson |
| 3,647,439 A | 3/1972 | Bass |
| 3,702,298 A | 11/1972 | Zsoldos |
| 3,929,678 A | 12/1975 | Laughlin et al. |
| 4,005,195 A | 1/1977 | Jandacek et al. |
| 4,005,196 A | 1/1977 | Jandacek et al. |
| 4,021,578 A | 5/1977 | Harich et al. |
| 4,055,655 A | 10/1977 | Maurer et al. |
| 4,104,190 A * | 8/1978 | Hartshorn .............. 252/187.21 |
| 4,180,473 A | 12/1979 | Muarer et al. |
| 4,264,592 A | 4/1981 | Xhajanka |
| 4,291,125 A | 9/1981 | Greatbatch |
| 4,297,374 A | 10/1981 | Wess |
| 4,385,632 A | 5/1983 | Odelhog |
| 4,564,461 A | 1/1986 | Skold et al. |
| 4,608,183 A | 8/1986 | Rossmoore |
| 4,666,616 A | 5/1987 | Rossmoore |
| 4,708,808 A | 11/1987 | Rossmoore |
| 4,753,821 A | 6/1988 | Giesecke et al. |
| 4,755,268 A | 7/1988 | Matsuo et al. |
| 4,780,216 A | 10/1988 | Wojtowicz |
| 4,797,300 A | 1/1989 | Jandacek et al. |
| 4,889,844 A | 12/1989 | Silvetti, Sr. et al. |
| 4,908,355 A | 3/1990 | Gettings et al. |
| 4,915,955 A | 4/1990 | Gomori |
| 4,933,178 A | 6/1990 | Capelli |
| 5,011,681 A | 4/1991 | Ciotti et al. |
| 5,017,295 A | 5/1991 | Antelman |
| 5,063,062 A | 11/1991 | Greenspan et al. |
| 5,073,382 A | 12/1991 | Antelman |
| 5,078,902 A | 1/1992 | Antelman |
| 5,081,106 A * | 1/1992 | Bentley et al. .................. 514/5 |
| 5,089,275 A | 2/1992 | Antelman |
| 5,177,065 A | 1/1993 | Silvetti, Sr. et al. |
| 5,236,698 A | 8/1993 | Richard et al. |
| 5,306,514 A | 4/1994 | Letton |
| 5,306,515 A | 4/1994 | Letton |
| 5,306,516 A | 4/1994 | Letton |
| 5,332,511 A | 7/1994 | Gay et al. |
| 5,332,568 A | 7/1994 | Raspanti |
| 5,338,539 A | 8/1994 | Raspanti |
| 5,362,714 A | 11/1994 | Radford et al. |
| 5,364,649 A | 11/1994 | Rossmoore et al. |
| 5,373,025 A | 12/1994 | Gay |
| 5,382,337 A | 1/1995 | Wlassics et al. |
| 5,464,559 A | 11/1995 | Marchin et al. |
| 5,503,840 A | 4/1996 | Jacobson et al. |
| 5,510,109 A | 4/1996 | Tomioka et al. |
| 5,518,713 A | 5/1996 | Raspanti |
| 5,520,906 A | 5/1996 | Stein et al. |
| 5,601,811 A | 2/1997 | Gallagher et al. |
| 5,660,840 A | 8/1997 | Pruett |
| 5,736,591 A | 4/1998 | Dunn |
| 5,820,918 A | 10/1998 | Ronan et al. |
| 5,962,517 A | 10/1999 | Murad |
| 6,017,461 A | 1/2000 | Garvey et al. |
| 6,139,823 A | 10/2000 | Dreschsler et al. |
| 6,181,963 B1 | 1/2001 | Chin et al. |
| 6,197,814 B1 * | 3/2001 | Arata ......................... 514/495 |

(Continued)

FOREIGN PATENT DOCUMENTS

EP          0507691 A       10/1992

(Continued)

OTHER PUBLICATIONS

Thomas Van Auken; "Solubility and Heat of Solution of Potassium dihydrogen citrate", J. Chem. Eng., 1991 36, p. 255-257.*

(Continued)

*Primary Examiner*—Humera N Sheikh
*Assistant Examiner*—Bethany Barham
(74) *Attorney, Agent, or Firm*—Morrison & Foerster LLP

(57) ABSTRACT

Anhydrous silver dihydrogen citrate compositions comprise silver dihydrogen citrate and citric acid. The anhydrous compositions can be prepared by freeze-drying. The anhydrous compositions can be reconstituted with a suitable diluent to form silver dihydrogen citrate compositions. The anhydrous compositions can be reconstituted and applied to a variety of substrates to impart an antimicrobial effect on the substrates.

18 Claims, No Drawings

U.S. PATENT DOCUMENTS

| | | | |
|---|---|---|---|
| 6,294,186 | B1 | 9/2001 | Beerse et al. |
| 6,387,355 | B2 | 5/2002 | Heidenfelder et al. |
| 6,409,995 | B1 | 6/2002 | Habeck et al. |
| 6,478,946 | B1 | 11/2002 | Westwood |
| 6,583,176 | B2 | 6/2003 | Arata |
| 6,605,751 | B1 | 8/2003 | Gibbins et al. |
| 6,692,773 | B2 | 2/2004 | Burrell et al. |
| 6,838,095 | B2 | 1/2005 | Newman et al. |
| 6,843,784 | B2 | 1/2005 | Modak et al. |
| 6,890,953 | B2 | 5/2005 | Arata |
| 7,026,308 | B1 | 4/2006 | Gavin et al. |
| 7,261,905 | B2 | 8/2007 | Arata |
| 2002/0016349 | A1 | 2/2002 | Heywang et al. |
| 2002/0192298 | A1 | 12/2002 | Burrell et al. |
| 2003/0198689 | A1 | 10/2003 | Arata |
| 2004/0044073 | A1 | 3/2004 | Arata |
| 2005/0202066 | A1 | 9/2005 | Arata |
| 2005/0245605 | A1 | 11/2005 | Arata |
| 2005/0247643 | A1 | 11/2005 | Arata |
| 2005/0274624 | A1 | 12/2005 | Arata |
| 2006/0051430 | A1 | 3/2006 | Arata et al. |
| 2006/0100273 | A1 | 5/2006 | Arata |
| 2006/0115440 | A1 | 6/2006 | Arata et al. |
| 2006/0188584 | A1 | 8/2006 | Arata |
| 2007/0269530 | A1 | 11/2007 | Arata |

FOREIGN PATENT DOCUMENTS

| | | |
|---|---|---|
| EP | 0517104 A | 12/1992 |
| EP | 0570838 A | 11/1993 |
| EP | 0582189 A | 2/1994 |
| EP | 0613893 A | 9/1994 |
| EP | 0709080 A | 5/1996 |
| EP | 1046391 | 10/2000 |
| EP | 1133980 | 9/2001 |
| EP | 1167358 | 1/2002 |
| GB | 1270410 | 4/1972 |
| GB | 2236117 | 3/1991 |
| JP | 47-32537 | 8/1972 |
| JP | 4-330007 | 11/1992 |
| WO | WO 93/17002 | 9/1993 |
| WO | WO 96/28390 | 9/1996 |
| WO | WO 97/00851 A | 1/1997 |
| WO | WO 99/18790 | 4/1999 |
| WO | WO 00/27390 | 5/2000 |
| WO | WO 2005/020915 A3 | 3/2005 |
| WO | WO 2005/041861 A3 | 5/2005 |
| WO | WO 2006/029213 A2 | 3/2006 |

OTHER PUBLICATIONS

Baxter S, "Evaluation of Axen® for Residual Activity," *Nelson Laboratories, Inc.*, Salt Lake City, Utah, 1-22 (Feb. 8, 2002).

Derwent Abstract, Accession No. 2000-268443, abstracting RU 2125971 (Feb. 10, 1999).

Derwent Abstract, Accession No. 2002-265533, abstracting RU 2179155 (Feb. 10, 2002).

IMS, "Axen® 30, Disinfectant, Fungicide & Virucide," *Manufactured by ETI H20*, a Division of Innovative Medical Services, El Cajon, CA.

IMS, "IMS Announces Positive Research Results of Anti-Bacterial Acne Ingredient," Press Release, *Innovative Medical Services*, El Cajon, Feb. 12, 2002.

Kawana R et al., "Inactivation of Human Viruses by Povidone-Iodine in Comparison with Other Antiseptics," *Dermatology*, 195(2):29-35 (1997).

Lin YE, Stout JE, Yu VL, "Experimental Results: Efficacy of Axenohol Solution in Eradicating *Legionella pneumophilal*," *Special Pathogens Laboratory*, VA Pittsburgh Healthcare System, Pittsburgh, PA 15240.

Mayer JL, "Accelerated Storage Stability of Axenohol and Axen," *EPL Bio-Analytical Services, Inc.*, Harristown, Illinois, 1-48 (May 8, 2000).

Miller JW, "Storage Stability of Axenohl and Axen Under Warehouse Conditions," *EPL Bio-Analytical Services, Inc.*, Harristown, Illinois 1-71 (Aug. 10, 2001).

Moore GE, "Acute Dermal Toxicity Study in Rats—Limit Test," *product safety labs*, East Brunswick, New Jersey, 1-14, (Oct. 21, 1999).

Moore GE, "Acute Oral Toxicity Study in Rats—Limit Test," *product safety labs*, East Brunswick, New Jersey, 1-14, (Oct. 21, 1999).

Moore GE, "Dermal Sensitization Study in Guinea Pigs (Buehler Method)," *product safety labs*, East Brunswick, New Jersey, 1-24, (Oct. 21, 1999).

Moore GE, "Primary Eye Irritation Study in Rabbits," *product safety labs*, East Brunswick, New Jersey, 1-1.5, (Oct. 6, 1999).

Moore GE, "Primary Eye Irritation Study in Rabbits," *product safety labs*, East Brunswick, New Jersey, 1-15, (Oct. 21, 1999).

Moore GE, "Primary Skin Irritation Study in Rabbits," *product safety labs*, East Brunswick, New Jersey, 1-15, (Oct. 21, 1999).

NLM, "PubChem Substance Summary" (PubChem Substance ID 679028) for "silver citrate," from the *National Center for Biotechnology Information* at the National Library of Medicine.

Product No. 006976, description of commercially available "silver citrate", from the online catalogue of *Crescent Chemical Company*, located at 1324 Motor Parkway, Islandia, New York 11749.

Product No. 3222, "silver nitrate" from the online catalogue of *ProChem, Inc.*, located at 826 Roosevelt Road, Rockford, IL 61109.

Richli P, Swiss 446691 (CLA 24b), "Preservatives for Tobacco," *Chemical Abstracts 69.8964n*, (Mar. 15, 1968, Appl. Apr. 22, 1964).

Srivastava GC et al., "Development of ready to use antiseptic dressings—Part 1. . . " *Labdev J. Scr. Tech.*, vol. 8-B (4):209-213, (Oct. 1970).

Tsimbler SM, Novikova LS (USSR), "Complexes of Silver (1) with some hydroxy acids," *Chemical Abstracts 87:74283n, ZH Neorg. Khim*, 22(7):1842-1846 (Russ) (1977).

U.S. Appl. No. 09/119,741, filed Jul. 21, 1998.

U.S. Appl. No. 60/107,710, filed Nov. 9, 1998.

Vaughan CD, "Solubility; Effects in Product, Package, Penetration, and Preservation," *Cosmetics and Toiletries*, 103:47-69 (Oct. 1988).

Yamamoto M, "Electrochemical removal of discoloration on silver product surface," (Chemical Yamamoto K.K.) Kokai Tokkyo Koho JP 04,297,599 (92,297,599), *Chemical Abstracts* 118:156836t (1993).

U.S. Appl. No. 10/936,465, filed Sep. 7, 2004, Arata, Non-Final Office Action, Jul. 5, 2006.

U.S. Appl. No. 10/936,465, filed Sep. 7, 2004, Arata, Amendment and Response, Jan. 8, 2007.

U.S. Appl. No. 10/936,465, filed Sep. 7, 2004, Arata, Final Office Action, Jun. 15, 2007.

U.S. Appl. No. 10/936,465, filed Sep. 7, 2004, Arata, Interview Summary, Oct. 16, 2007.

U.S. Appl. No. 10/936,465, filed Sep. 7, 2004, Arata, Response and Amendment After Final, Nov. 15, 2007.

U.S. Appl. No. 10/936,465, filed Sep. 7, 2004, Arata, Non-Final Office Action, Jan. 9, 2008.

U.S. Appl. No. 10/936,465, filed Sep. 7, 2004, Arata, Response and Amendment, Jul. 9, 2008.

U.S. Appl. No. 11/144,398, filed Jun. 3, 2005, Arata, Non-Final Office Action, Jun. 29, 2006.

U.S. Appl. No. 11/144,398, filed Jun. 3, 2005, Arata, Amendment and Response, Jan. 3, 2007.

U.S. Appl. No. 11/144,398, filed Jun. 3, 2005, Arata, Final Office Action, Mar. 27, 2007.

U.S. Appl. No. 11/144,398, filed Jun. 3, 2005, Arata, Response and Amendment After Final, Sep. 26, 2007.

U.S. Appl. No. 11/144,398, filed Jun. 3, 2005, Arata, Duty of Candor, Oct. 4, 2007.

U.S. Appl. No. 11/144,398, filed Jun. 3, 2005, Arata, Interview Summary, Oct. 16, 2007.

U.S. Appl. No. 11/144,398, filed Jun. 3, 2005, Arata, Supplemental Response and Amendment, Dec. 10, 2007.

U.S. Appl. No. 11/144,398, filed Jun. 3, 2005, Arata, Non-Final Office Action, Jan. 2, 2008.

U.S. Appl. No. 11/144,398, filed Jun. 3, 2005, Arata, Response and Amendment, Jul. 1, 2008.
U.S. Appl. No. 10/232,499, filed Aug. 31, 2002, Arata, Non-Final Office Action, Jan. 18, 2005.
U.S. Appl. No. 10/232,499, filed Aug. 31, 2002, Arata, Amendment, Jul. 18, 2005.
U.S. Appl. No. 10/232,499, filed Aug. 31, 2002, Arata, Final Office Action, Oct. 20, 2005.
U.S. Appl. No. 10/232,499, filed Aug. 31, 2002, Arata, Notice of Abandonment, Apr. 28, 2006.
U.S. Appl. No. 10/232,499, filed Aug. 31, 2002, Arata, Examiner Interview Summary Record, May 17, 2006.
U.S. Appl. No. 11/407,654, filed Apr. 20, 2006, Arata, Preliminary Amendment, Apr. 20, 2006.
U.S. Appl. No. 11/407,654, filed Apr. 20, 2006, Arata, Preliminary Amendment, Aug. 18, 2006.
U.S. Appl. No. 11/407,654, filed Apr. 20, 2006, Arata, Non-Final Rejection, Jun. 20, 2008.
U.S. Appl. No. 11/407,654, filed Apr. 20, 2006, Arata, Abandonment, Jan. 15, 2009.
U.S. Appl. No. 11/407,654, filed Apr. 20, 2006, Arata, Examiner Interview Summary Record, Jan. 15, 2009.
U.S. Appl. No. 12/340,231, filed Dec. 19, 2008, Arata, Preliminary Amendment, Dec. 19, 2008.
U.S. Appl. No. 10/928,638, filed Aug. 27, 2004, Arata, Interview Summary, Nov. 18, 2005.
U.S. Appl. No. 10/928,638, filed Aug. 27, 2004, Arata, Non-Final Office Action, Nov. 28, 2005.
U.S. Appl. No. 10/928,638, filed Aug. 27, 2004, Arata, Interview Summary, Jun. 21, 2006.
U.S. Appl. No. 10/928,638, filed Aug. 27, 2004, Arata, Office Communication—Notice of Abandonment, Jun. 28, 2006.
U.S. Appl. No. 10/928,639, filed Aug. 27, 2004, Arata, Non-Final Office Action, Jul. 5, 2006.
U.S. Appl. No. 10/928,639, filed Aug. 27, 2004, Arata, Amendment and Response, Jan. 8, 2007.
U.S. Appl. No. 10/928,639, filed Aug. 27, 2004, Arata, Final Office Action, Jun. 15, 2007.
U.S. Appl. No. 10/928,639, filed Aug. 27, 2004, Arata, Interview Summary, Oct. 16, 2007.
U.S. Appl. No. 10/928,639, filed Aug. 27, 2004, Arata, Response and Amendment After Final, Nov. 19, 2007.
U.S. Appl. No. 10/928,639, filed Aug. 27, 2004, Arata, Non-Final Office Action, Jan. 9, 2008.
U.S. Appl. No. 10/928,639, filed Aug. 27, 2004, Arata, Notice of Appeal Filed, Jul. 9, 2008.
U.S. Appl. No. 10/928,639, filed Aug. 27, 2004, Arata, Applicant Arguments/Remarks Made in an Amendment, Oct. 9, 2008.
U.S. Appl. No. 10/928,639, filed Aug. 27, 2004, Arata, Final Rejection, Dec. 29, 2008.
U.S. Appl. No. 11/298,130, filed Dec. 8, 2005, Arata, Preliminary Amendment, Dec. 8, 2005.
U.S. Appl. No. 11/298,130, filed Dec. 8, 2005, Arata, Non-Final Office Action, Apr. 27, 2006.
U.S. Appl. No. 11/298,130, filed Dec. 8, 2005, Arata, Amendment and Election Under Restriction/Election Requirement, Jul. 31, 2006.
U.S. Appl. No. 11/298,130, filed Dec. 8, 2005, Arata, Non-Final Office Action, Sep. 27, 2006.
U.S. Appl. No. 11/298,130, filed Dec. 8, 2005, Arata, Office Communication—Notice of Abandonment, Apr. 26, 2007.
U.S. Appl. No. 10/103,548, filed Mar. 20, 2002, Arata, Non-Final Office Action, Jul. 1, 2003.
U.S. Appl. No. 10/103,548, filed Mar. 20, 2002, Arata, Interview Summary, Aug. 26, 2003.
U.S. Appl. No. 10/103,548, filed Mar. 20, 2002, Arata, Amendment A, Dec. 5, 2003.
U.S. Appl. No. 10/103,548, filed Mar. 20, 2002, Arata, Office Communication—Notice of Non-Compliant Amendment, Dec. 24, 2003.
U.S. Appl. No. 10/103,548, filed Mar. 20, 2002, Arata, Amendment A—Corrected, Jan. 26, 2004.
U.S. Appl. No. 10/103,548, filed Mar. 20, 2002, Arata, Final Office Action, May 18, 2004.
U.S. Appl. No. 10/103,548, filed Mar. 20, 2002, Arata, Amendment, Sep. 22, 2004.
U.S. Appl. No. 10/103,548, filed Mar. 20, 2002, Arata, Interview Summary, Oct. 15, 2004.
U.S. Appl. No. 10/103,548, filed Mar. 20, 2002, Arata, Advisory Action, Oct. 19, 2004.
U.S. Appl. No. 10/103,548, filed Mar. 20, 2002, Arata, Response Under 37 C.F.R. § 1.116, Nov. 19, 2004.
U.S. Appl. No. 10/103,548, filed Mar. 20, 2002, Arata, Notice of Allowance, Dec. 18, 2004.
U.S. Appl. No. 11/125,849, filed May 9, 2005, Arata, Preliminary Amendment, May 9, 2005.
U.S. Appl. No. 11/125,849, filed May 9, 2005, Arata, Non-Final Office Action, Aug. 1, 2006.
U.S. Appl. No. 11/125,849, filed May 9, 2005, Arata, Amendment and Response, Feb. 5, 2007.
U.S. Appl. No. 11/125,849, filed May 9, 2005, Arata, Office Communication, Apr. 19, 2007.
U.S. Appl. No. 11/125,849, filed May 9, 2005, Arata, Amendment and Response, Jun. 11, 2007.
U.S. Appl. No. 11/125,849, filed May 9, 2005, Arata, Supplemental Response, Aug. 27, 2007.
U.S. Appl. No. 11/125,849, filed May 9, 2005, Arata, Duty of Candor, Oct. 9, 2007.
U.S. Appl. No. 11/125,849, filed May 9, 2005, Arata, Final Office Action, Nov. 16, 2007.
U.S. Appl. No. 11/125,849, filed May 9, 2005, Arata, Amendment and Response to Final Office Action and Request for Continued Examination, May 15, 2008.
U.S. Appl. No. 11/125,849, filed May 9, 2005, Arata, Non-Final Office Rejection, Aug. 12, 2008.
U.S. Appl. No. 11/125,849, filed May 9, 2005, Arata, Amendment/Req. Reconsideration-After Non-Final Reject, Feb. 12, 2009.
U.S. Appl. No. 10,434,742, filed May 9, 2003, Arata, Office Communication—Restriction Requirement, Nov. 19, 2003.
U.S. Appl. No. 10,434,742, filed May 9, 2003, Arata, Election of Species, Jan. 15, 2004.
U.S. Appl. No. 10,434,742, filed May 9, 2003, Arata, Non-Final Office Action, May 11, 2005.
U.S. Appl. No. 10,434,742, filed May 9, 2003, Arata, Amendment, Nov. 14, 2005.
U.S. Appl. No. 10,434,742, filed May 9, 2003, Arata, Office Communication, Feb. 7, 2006.
U.S. Appl. No. 10,434,742, filed May 9, 2003, Arata, Response to Communication, Aug. 4, 2006.
U.S. Appl. No. 10,434,742, filed May 9, 2003, Arata, Final Office Action, Oct. 20, 2006.
U.S. Appl. No. 10,434,742, filed May 9, 2003, Arata, Amendment and Response After Final Office Action, Mar. 23, 2007.
U.S. Appl. No. 10,434,742, filed May 9, 2003, Arata, Notice of Allowance, Apr. 19, 2007.
U.S. Appl. No. 10,434,742, filed May 9, 2003, Arata, Issue Notification, Aug. 8, 2007.
U.S. Appl. No. 11,832,474, filed Aug. 1, 2007, Arata, Preliminary Amendment, Aug. 1, 2007.
U.S. Appl. No. 11,832,474, filed Aug. 1, 2007, Arata, Duty of Candor, Oct. 3, 2007.
U.S. Appl. No. 11,832,474, filed Aug. 1, 2007, Arata, Interview Summary, Oct. 15, 2007.
U.S. Appl. No. 10,600,006, filed Jun. 19, 2003, Arata, Non-Final Office Actionl—Restriction Requirement, Dec. 8, 2004.
U.S. Appl. No. 10,600,006, filed Jun. 19, 2003, Arata, Response to Restriction Requirement, Jun. 7, 2005.
U.S. Appl. No. 10,600,006, filed Jun. 19, 2003, Arata, Non-Final Office Action, Aug. 12, 2005.
U.S. Appl. No. 10,600,006, filed Jun. 19, 2003, Arata, Amendment, Feb. 13, 2006.
U.S. Appl. No. 10,600,006, filed Jun. 19, 2003, Arata, Final Office Action, Apr. 28, 2006.
U.S. Appl. No. 10,600,006, filed Jun. 19, 2003, Arata, Interview Summary, May 6, 2006.
U.S. Appl. No. 10,600,006, filed Jun. 19, 2003, Arata, Amendment and Response to Office Action, Mar. 27, 2007.

U.S. Appl. No. 10/600,006, filed Jun. 19, 2003, Arata, Non-Final Office Action, Jun. 22, 2007.
U.S. Appl. No. 10/600,006, filed Jun. 19, 2003, Arata, Duty of Candor, Oct. 9, 2007.
U.S. Appl. No. 10/600,006, filed Jun. 19, 2003, Arata, Interview Summary, Oct. 15, 2007.
U.S. Appl. No. 10/600,006, filed Jun. 19, 2003, Arata, Amendment and Response to Office Action, Dec. 26, 2007.
U.S. Appl. No. 10/600,006, filed Jun. 19, 2003, Arata, Final Office Action, Apr. 1, 2008.
U.S. Appl. No. 10/600,006, filed Jun. 19, 2003, Arata, Notice of Appeal Filed, Oct. 1, 2008.
U.S. Appl. No. 11/060,013, filed Feb. 16, 2005, Arata, Preliminary Amendment, Feb. 16, 2005.
U.S. Appl. No. 11/060,013, filed Feb. 16, 2005, Arata, Requirement for Restriction/Election, Jul. 31, 2006.
U.S. Appl. No. 11/060,013, filed Feb. 16, 2005, Arata, Response to Election / Restriction Filed, Dec. 4, 2006.
U.S. Appl. No. 11/060,013, filed Feb. 16, 2005, Arata, Amendment/Req. Reconsideration-After Non-Final Reject, Mar. 22, 2007.
U.S. Appl. No. 11/060,013, filed Feb. 16, 2005, Arata, Non-Final Rejection, May 16, 2007.
U.S. Appl. No. 11/060,013, filed Feb. 16, 2005, Arata, Duty of Candor, Oct. 3, 2007.
U.S. Appl. No. 11/060,013, filed Feb. 16, 2005, Arata, Examiner Interview Summary Record (PTOL—413), Oct. 16, 2007.
U.S. Appl. No. 11/060,013, filed Feb. 16, 2005, Arata, Amendment/Req. Reconsideration-After Non -Final Reject, Nov. 16, 2007.
U.S. Appl. No. 11/060,013, filed Feb. 16, 2005, Arata, Notice of Allowance and Fees Due (PTOL-85), Jan. 7, 2008.
U.S. Appl. No. 11/060,013, filed Feb. 16, 2005, Arata, Examiner Interview Summary Record (PTOL—413), Jan. 7, 2008.
U.S. Appl. No. 11/060,013, filed Feb. 16, 2005, Arata, Notice of Allowance and Fees Due (PTOL-85), Jun. 4, 2008.
U.S. Appl. No. 11/060,013, filed Feb. 16, 2005, Arata, Issue Notification, Sep. 24, 2008.
U.S. Appl. No. 12/204,374, filed Sep. 4, 2008, Arata, Preliminary Amendment, Sep. 4, 2008.
CN 200580037477.6, filed Apr. 29, 2007, Arata, Amended claims, Mar. 21, 2008.
CR 9029, filed Mar. 2, 2007, Arata, Opposition filed by Gustavo M. Umana, Oct. 27, 2008.
EA 200700579, filed Apr. 6, 2007, Arata, Office Action Response, Nov. 1, 2008.
EA 200700579, filed Apr. 6, 2007, Arata, Office Action, Apr. 24, 2008.
MX MX/a/2007/002762, filed Mar. 7, 2007, Arata, Response to Office Action , Jul. 10, 2007.
PCT PCT/US2005/031876, filed Sep. 6, 2005, Arata, Written Opinion of the International Searching Authority, Apr. 3, 2007.
PCT PCT/US2005/031876, filed Sep. 6, 2005, Arata, International Preliminary Report on Patentability, May 1, 2007.
SG 200701618-1, filed Mar. 2, 2007, Arata, Written Opinion, Sep. 5, 2008.
SG 200701618-1, filed Mar. 2, 2007, Arata, Response to Written Opinion, Feb. 5, 2009.
CN 200480024459.X, filed Feb. 27, 2006, Arata, Office Action, May 25, 2007.
CN 200480024459.X, filed Feb. 27, 2006, Arata, Office Action response, Dec. 5, 2007.
CN 200480024459.X, filed Feb. 27, 2006, Arata, Decision of Rejection, Mar. 17, 2008.
CN 200480024459.X, filed Feb. 27, 2006, Arata, Request for Reexamination, Feb. 15, 2008.
MX PA/a/2006/002283, filed Feb. 28, 2006, Arata, Office Action, Mar. 31, 2008.
MX PA/a/2006/002283, filed Feb. 28, 2006, Arata, Office Action Response, Aug. 6, 2008.
MX PA/a/2006/002283, filed Feb. 28, 2006, Arata, Office Action, Sep. 11, 2008.
MX PA/a/2006/002284, filed Feb. 28, 2006, Arata, Amendment, Jul. 11, 2007.
NZ 545932, filed Mar. 15, 2006, Arata, Office Action, May 15, 2008.
NZ 545933, filed Mar. 15, 2006, Arata, Office Action, May 30, 2008.
PCT PCT/US2004/027901, filed Aug. 27, 2004, Arata, Int'l Search / Written Opinion, Aug. 9, 2005.
PCT PCT/US2004/027901, filed Aug. 27, 2004, Arata, International Prelim. Report on Patentability, Feb. 28, 2006.
SG 200601193-6, filed Feb. 23, 2006, Arata, Notification of Grant, Dec. 31, 2008.
SG 200601197-7, filed Feb. 23, 2006, Arata, Certificate of Grant of Patent, Sep. 30, 2008.
ZA 2006/02542, Mar. 28, 2006, Arata, Patent Certificate, Sep. 26, 2007.
ZA 2006/02543, filed Mar. 28, 2006, Arata, Patent Certificate, Mar. 26, 2008.
AP AP/P/00/01783, filed Oct. 9, 1998, Arata, Examination, Mar. 13, 2003.
AP AP/P/00/01783, filed Oct. 9, 1998, Arata, Grant of Patent, Jun. 8, 2005.
AU 11880/99, filed Oct. 9, 1998, Arata, Examination, Dec. 5, 2000.
AU 11880/99, filed Oct. 9, 1998, Arata, Response to Examination, Aug. 12, 2002.
CA 2305139, filed Oct. 9, 1998, Arata, First Office Action, Jun. 13, 2006.
CA 2305139, filed Oct. 9, 1998, Arata, Amendment/Remarks After Examiner's Report, Dec. 13, 2006.
CA 2305139, filed Oct. 9, 1998, Arata, Office Action, May 14, 2007.
CA 2305139, filed Oct. 9, 1998, Arata, Amendment/Remarks After Examiner's Report, Nov. 14, 2007.
CA 2305139, filed Oct. 9, 1998, Arata, Notice of Allowance, Feb. 25, 2008.
CN 98812103.4, filed Oct. 9, 1998, Arata, First Office Action, Aug. 22, 2003.
CN 98812103.4, filed Oct. 9, 1998, Arata, Response to First Office Action, Mar. 4, 2004.
CN 98812103.4, filed Oct. 9, 1998, Arata, Second Office Action, May 14, 2004.
CN 98812103.4, filed Oct. 9, 1998, Arata, Response to Second Office Action, Sep. 27, 2004.
CN 98812103.4, filed Oct. 9, 1998, Arata, Third Office Action, Feb. 25, 2005.
CN 98812103.4, filed Oct. 9, 1998, Arata, Response to Third Office Action, Jul. 12, 2005.
CN 98812103.4, filed Oct. 9, 1998, Arata, Fourth Office Action, Dec. 9, 2005.
CN 98812103.4, filed Oct. 9, 1998, Arata, Response to Fourth Office Action, Apr. 21, 2006.
CN 98812103.4, filed Oct. 9, 1998, Arata, Decision on Rejection, Jan. 19, 2007.
CN 98812103.4, filed Oct. 9, 1998, Arata, Request for Examination, May 8, 2007.
CN 98812103.4, filed Oct. 9, 1998, Arata, Notice of Examination, Jul. 18, 2008.
CN 98812103.4, filed Oct. 9, 1998, Arata, Response to Reexamination, Oct. 20, 2008.
CN 98812103.4, filed Oct. 9, 1998, Arata, Rejection Reversed, Dec. 23, 2008.
CN 200410045711.7, filed May 21, 2004, Arata, First Office Action, Jun. 10, 2005.
CN 200410045711.7, filed May 21, 2004, Arata, Decision on Rejection, Jun. 9, 2006.
CN 200410045711.7, filed May 21, 2004, Arata, Response to Decision on Rejection, Sep. 25, 2006.
CN 200410045711.7, filed May 21, 2004, Arata, Reexamination Decision, Oct. 22, 2008.
CN 200410045711.7, filed May 21, 2004, Arata, Decision to Grant, Feb. 6, 2009.
CN 200410045710.2, filed May 21, 2004, Arata, First Office Action, Aug. 18, 2006.
CN 200410045709.X, filed May 21, 2004, Arata, First Office Action, Jun. 29, 2005.
CN 200410045709.X, filed May 21, 2004, Arata, Decision to Grant, Sep. 1, 2006.
CN 200410045709.X, filed May 21, 2004, Arata, Granted Claims in English, Sep. 1, 2006.

EP 98954966.2, filed Oct. 9, 1998, Arata, International Preliminary Exam Report, Jun. 9, 2000.

EP 98954966.2, filed Oct. 9, 1998, Arata, First Exam Report, Jul. 24, 2006.

EP 98954966.2, filed Oct. 9, 1998, Arata, Response to Exam, Jan. 30, 2007.

EP 98954966.2, filed Oct. 9, 1998, Arata, Notice of Allowance, Apr. 10, 2004.

EP 98954966.2, filed Oct. 9, 1998, Arata, Decision to Grant, Nov. 14, 2007.

EP 98954966.2, filed Oct. 9, 1998, Arata, Notice of opposition, Oct. 9, 2008.

NZ 503582, filed Oct. 9, 1998, Arata, Examination Report, May 13, 2002.

NZ 503582, filed Oct. 9, 1998, Arata, Examination Report, Sep. 6, 2002.

NZ 503582, filed Oct. 9, 1998, Arata, Grant of Patent, Mar. 31, 2003.

NZ 518845, May 8, 2002, Arata, Grant of Patent, Jun. 8, 2004.

PCT PCT/US98/21604, filed Oct. 9, 1998, Arata, Written Opinion, Oct. 27, 1999.

PCT PCT/US98/21604, filed Oct. 9, 1998, Arata, International Preliminary Exam Report, Mar. 22, 2000.

Kawana R et al., "Inactivation of Human Viruses by Povidone-Iodine in Comparison with Other Antiseptics," *Dermatology*, 195(2):29-35 (1997).

Mayer JL, "Accelerated Storage Stability of Axenohol and Axen," *EPL Bio-Analytical Services, Inc.*, Harristown, Illinois, 1-48 (May 8, 2000).

Miller JW, "Storage Stability of Axenohl and Axen Under Warehouse Conditions," *EPL Bio-Analytical Services, Inc.*, Harristown, Illinois 1-71 (Aug. 10, 2001).

Moore GE, "Acute Dermal Toxicity Study in Rats—Limit Test," *product safety labs*, East Brunswick, New Jersey, 1-14, (Oct. 21, 1999).

Moore GE, "Acute Oral Toxicity Study in Rats—Limit Test," *product safety labs*, East Brunswick, New Jersey, 1-14, (Oct. 21, 1999).

Moore GE, "Dermal Sensitization Study in Guinea Pigs (Buehler Method)," *product safety labs*, East Brunswick, New Jersey, 1-24, (Oct. 21, 1999).

Moore GE, "Primary Eye Irritation Study in Rabbits," *product safety labs*, East Brunswick, New Jersey, 1-15, (Oct. 6, 1999).

Moore GE, "Primary Eye Irritation Study in Rabbits," *product safety labs*, East Brunswick, New Jersey, 1-15, (Oct. 21, 1999).

Moore GE, "Primary Skin Irritation Study in Rabbits," *product safety labs*, East Brunswick, New Jersey, 1-15, (Oct. 21, 1999).

Richli P, Swiss 446691 (CL.A 24b), "Preservatives for Tobacco," *Chemical Abstracts 69.8964n*, (Mar. 15, 1968, Appl. Apr. 22, 1964).

Srivastava GC et al., "Development of ready to use antiseptic dressings—Part 1 . . . " *Labdev J. Scr. Tech.*, vol. 8-B (4):209-213, (Oct. 1970).

Tsimbler SM, Novikova LS (USSR), "Complexes of Silver (1) with some hydroxy acids," *Chemical Abstracts 87:74283n, ZH Neorg. Khim*, 22(7):1842-1846 (Russ) (1977).

Vaughan CD, "Solubility; Effects in Product, Package, Penetration, and Preservation," *Cosmetics and Toiletries*, 103:47-69 (Oct. 1988).

Yamamoto M, "Electrochemical removal of discoloration on silver product surface," (Chemical Yamamoto K.K.) Kokai Tokkyo Koho JP 04,297,599 (92,297,599), *Chemical Abstracts* 118:156836t (1993).

\* cited by examiner

ANHYDROUS SILVER DIHYDROGEN CITRATE COMPOSITIONS

This application is a continuation of U.S. application Ser. No. 11/298,130, filed Dec. 8, 2005, now abandoned, which is a continuation of U.S. application Ser. No. 10/928,638, filed Aug. 27, 2004, now abandoned, which claims priority from U.S. provisional application Ser. No. 60/498,347, filed Aug. 28, 2003, each of which is incorporated herein by reference in its entirety.

FIELD OF THE INVENTION

This invention generally relates to antimicrobial compositions. In particular, the invention provides compositions comprising anhydrous silver dihydrogen citrate and citric acid, processes of making the compositions and antimicrobial methods of using the solid compositions.

BACKGROUND OF THE INVENTION

Antimicrobial metal ion solutions have been used as disinfectants. Silver solutions have been used as disinfectants in cooling towers, swimming pools, hot water systems in hospitals, portable water systems and spa pools. Additionally, silver ion solutions have been prepared for the treatment of wounds, however the silver ions used in the proposed methods are unstable and must be generated near the wound in order to deliver a therapeutic dose to the wound site.

Silver salts, such as silver citrate salts, have also been proposed as antimicrobial dusting agents. However, these dusting agents must be kept dry and are generally not convenient for imparting preservative value to consumer products or for delivering antimicrobial effects to an end user or to the environment of the end user. Colloidal silver has found a variety of uses, including: as a wood preservative; as a disinfectant of food and beverage containers and industrial processing equipment; as a bactericide in paints; as a biocide in synthetic polymer films; and as a sterilizing agent in bandages.

Aqueous solutions of silver dihydrogen citrate and citric acid have been disclosed in U.S. Pat. No. 6,197,814 (incorporated herein in its entirety) as disinfectants in a variety of settings. These water solutions of silver dihydrogen citrate and citric acid are made by passing an electrical current through a pair of silver electrodes that are immersed in a water solution of citric acid. These silver dihydrogen citrate solutions are effective against a wide-variety of microbes, including bacteria, viruses and fungi, and are non-toxic in the human environment at concentrations effective to combat microbial infestation. However, aqueous solutions are bulky and heavy, and are thus uneconomical to store and to transport.

There is a need for silver dihydrogen citrate compositions that can be economically stored, transported or both. Such compositions should be substantially free of water in order to minimize the space required for their storage, as well to minimize their shipping weight. Such compositions should confer the same beneficial antimicrobial effect as solutions of silver dihydrogen citrate when combined with water or other aqueous solution. The present invention satisfies this need and provides related advantages as well.

SUMMARY OF THE INVENTION

The present invention provides compositions comprising anhydrous silver dihydrogen citrate and citric acid and a process of making said compositions. The process includes freezing a stock solution of aqueous silver dihydrogen citrate and then freeze-drying the frozen stock solution to produce anhydrous silver dihydrogen citrate.

The invention further provides a method of using anhydrous silver dihydrogen citrate and citric acid by combining it with an aqueous diluent to produce an antimicrobially effective aqueous silver dihydrogen citrate solution.

DETAILED DESCRIPTION OF THE INVENTION

The invention provides compositions comprising anhydrous silver dihydrogen citrate and citric acid. Surprisingly, it has been found that the anhydrous silver dihydrogen citrate compositions may be reconstituted after a period of time to make stable silver dihydrogen citrate solutions having effective antimicrobial activity. The anhydrous compositions offer the advantage of ease and economy of storage. They also offer the advantage of being more economical to transport than aqueous solutions of silver dihydrogen citrate. As the anhydrous compositions may be conveniently reconstituted with water or another aqueous diluent, the anhydrous compositions offer a convenient alternative to aqueous solutions of silver dihydrogen citrate.

Silver dihydrogen citrate has been identified as the active antimicrobial ingredient in a solution produced by electrolysis of silver electrodes immersed in a citric acid electrolyte solution. The structure of silver dihydrogen citrate can be represented by formula I:

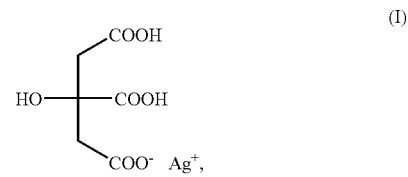

wherein $Ag^+$ is silver ion and the negatively charged carbonate ($COO^-$) is the most likely charged group in the dihydrogen citrate moiety. The chemical formula for this complex is $AgC_6H_7O_7$, and its molecular weight is 298.99 g/mol. As can be seen from the formula above, silver dihydrogen citrate is a salt, wherein the silver ion is the cation and the dihydrogen citrate ion is the anion. In solution, the salt is present in a dissociated state, the cation and anion being surrounded by water molecules, which associate with the ions through their polar OH groups.

Citric acid can be represented by formula II:

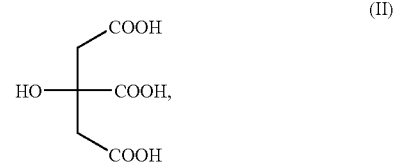

having a chemical formula of $C_6H_8O_7$ and a molecular weight of 192.13 g/mol. Citric acid is readily available from commercial sources. Citric acid is very soluble in water. Aqueous solutions of citric acid may be up to about 60% (wt/vol) citric acid in water at 25° C.

The invention also provides methods of making solid silver dihydrogen citrate compositions. The method starts with providing a stock solution of silver dihydrogen citrate, as described in U.S. Pat. No. 6,197,814. A summary of the process of making the silver dihydrogen citrate solution is as follows.

A process of making the stock solution of silver dihydrogen citrate is an electrolytic process. The process begins with preparation of an electrolyte solution, which is an aqueous solution comprising citric acid. It has been found that citric acid solutions having citric acid concentrations in the range of about 1% (wt./vol.) to about the solubility limit of citric acid in water (about 60% wt./vol.) are suitable for preparing silver dihydrogen citrate solutions. In some embodiments, the range is about 5 to about 25 wt % citric acid, with specific values, being 10, 15 and 20 wt %. The electrolyte may comprise other ingredients that will not interfere with the electrolytic process.

A pair of silver electrodes are immersed into the electrolyte solution at a suitable spacing to allow ionic current flow between them. A suitable spacing is greater than about 2 mm, for example from about 2 to about 8 mm. An electrolytic potential is applied across the electrodes to create an ionic current flow between the electrodes. While it is possible to use a D.C. power supply to apply the electrolytic potential, it has been found desirable to apply an alternating wave form to the electrodes. A suitable voltage is about 12 to about 50 volts. A suitable alternating waveform applies a pulsed potential having a peak voltage of about 12 to 50 volts to the electrodes, with periodic intermittent phase reversal. The resulting flow of ions through the electrolyte solution results in production of an aqueous solution of silver dihydrogen citrate and citric acid. This solution may be further processed, for example by settling, filtration or both, before being used in the process of making anhydrous silver dihydrogen citrate.

It is possible to perform the foregoing process batch-wise or in a continuous process. It is also possible to recirculate silver dihydrogen citrate solution through the electrolytic cell to increase the final concentration of silver dihydrogen citrate in the solution. The person of skill in the art will recognize that the foregoing steps may be practiced in a number of different variations known in the art. The process is described in fuller detail in U.S. Pat. No. 6,197,814 (incorporated by reference) and in the examples below. The resulting solution is referred to herein as the "stock solution," meaning a water solution of silver dihydrogen citrate and citric acid that has not yet been subjected to freeze-drying.

Having provided the stock solution, the next step is to remove water from the stock solution to produce anhydrous silver dihydrogen citrate. It has been found that freeze-drying results in a superior product. In the freeze-drying process, a frozen solution comprising silver dihydrogen citrate and citric acid solution is subjected to a vacuum, whereby the temperature and pressure of the solution are reduced below the triple point of water. Below the triple point, water will sublimate, passing directly from the solid phase into the gaseous phase. In some embodiments, the solution is first frozen, then placed in a freeze-drying apparatus. The solution may be frozen, for example, by placing it in a cold environment such as a freezer. In other embodiments, the solution is placed in the freeze-drying apparatus and then frozen. As evaporation is an endothermic process, the solution may be frozen by placing it in the freeze-drying apparatus and applying the vacuum. As water evaporates from the solution sample, it draws heat from the sample, thereby lowering the sample's temperature to below the triple point of the sample. In such cases, it is useful to take measures, such as centrifugation, to prevent foaming of the sample. It is also useful to heat the sample during the freeze-drying process in order to compensate for the latent heat deficit of the frozen solution caused by sublimation of water. The person skilled in the art will recognize that heating the frozen sample will generally speed the freeze-drying process, so long as the sample's temperature remains below the triple point of the solution.

Freeze-drying apparatuses are known and available from a number of suppliers; or they may be constructed using procedures known in the art. A freeze-drying apparatus comprises a drying chamber, a condenser to trap water of sublimation, a cooling system that supplies refrigerant to the vacuum chamber and the condenser, a vacuum system to apply a vacuum to the drying chamber. The freeze-drying apparatus may also have a temperature control device that allows one to cool the sample to the freezing point and to heat the sample to speed the sublimation process. The temperature control device will in some cases include refrigeration coils that circulate refrigerant. The temperature control device may also include heating coils or another appropriate device to heat the sample during the freeze-drying process.

The freeze-drying process removes sufficient water to form an anhydrous composition comprising silver dihydrogen citrate and citric acid. The anhydrous silver dihydrogen citrate crystals ate translucent-gray in color. In some embodiments, these crystals are ground to a fine powder and stored for an indefinite period of time until they are reconstituted In some embodiments, the powder is stored in a light-proof container, such as an opaque bottle or in a light-proof box to prevent decomposition by light.

Surprisingly it has been found that a silver dihydrogen citrate composition reconstituted using the same volume of diluent, such as water, as was present in the stock solution possesses the same concentration of free silver ion as was in the stock solution, without any noticeable degradation, reduction of the redox state of silver, or formation of colloid. As silver ion is the active antimicrobial agent in a silver dihydrogen citrate composition, such reconstituted compositions are expected to possess the same antimicrobial properties as the stock solution. The reconstituted compositions may thus be used in any manner that the stock solutions could have been used.

The term "composition comprising anhydrous silver dihydrogen citrate and citric acid" means a solid composition containing silver dihydrogen citrate and citric acid. Thus, while the composition may contain detectable quantities of water, it does not contain enough water for the composition to be fluid. While the solid composition may be amorphous or crystalline, a crystalline form is especially desirable, as such is formed by the freeze-drying process described, and is considered especially stable. Thus, the invention further provides crystalline compositions comprising anhydrous silver dihydrogen citrate and citric acid.

The invention further provides anhydrous silver dihydrogen citrate compositions that are substantially free of water. The term "substantially free" means that the sample comprises less than the lower detectable limit of water. While it is theoretically possible to remove all water from the sample, in some cases it is sufficient to dry the sample to the point that the amount of remaining water, if any, is below the detection limit for art-recognized detection means. Some detection means that may be mentioned are gas chromatography (GC), nuclear magnetic resonance spectrometry (NMR), mass spectrometry (MS), or combinations of two or more thereof, for example GC-MS.

The invention further provides anhydrous silver dihydrogen citrate containing an amount of water above the detection limit of water by conventional testing processes. In such embodiments, it is preferred that the anhydrous silver dihydrogen citrate comprises less than about 2%, in particular less than about 1%, more particularly less than about 0.5% and even more particularly less than about 0.1% water (wt./wt. %). The person skilled in the art will recognize that such anhydrous compositions may be obtained by performing the freeze-drying process under conditions, such as vacuum, length of time and heating, sufficient to remove the appropriate amount of water from the frozen sample.

The invention further provides compositions comprising anhydrous silver dihydrogen citrate and a molar excess of citric acid. The term "molar excess" means an amount of citric acid such that, for each mole of silver dihydrogen citrate in the composition, there is greater than one mole of citric acid. For example, a 1-60% wt/vol solution of citric acid that has been subjected to electrolysis as previously describe will contain from about 0.00001 to about 1 wt % silver ion. In a particular example, a 10% citric acid solution treated by the electrolysis process described above contains about 0.1% silver ion. The person of skill in the art will recognize that there is a molar excess of citric acid to silver dihydrogen citrate in the solution. In this example, the molar excess is about 15 fold. The person of skill in the art will further recognize that, as citric acid is non-volatile, the solid silver dihydrogen citrate composition produced by the foregoing freeze-drying process will contain a molar excess of citric acid over silver dihydrogen citrate. In some embodiments, this molar excess is from about 5 to about 10,000 fold; in particular about 8 to about 10,000 fold. It is believed that an excess of citric acid over silver dihydrogen citrate of greater than about 5, more particularly greater than about 10, and even more particularly greater than about 12, provides substantial stability of the silver dihydrogen citrate complex in solution. Thus, the invention provides solid silver dihydrogen citrate compositions comprising silver dihydrogen citrate and greater than about 5-, in particular at least about 8-, more particularly at least about 10-, and even more particularly at least about 12-fold molar excess of citric acid over silver dihydrogen citrate.

It has surprisingly been found that anhydrous silver dihydrogen citrate compositions are capable of being reconstituted to produce an antimicrobially active composition. It has not been previously reported that an anhydrous silver dihydrogen citrate composition would dissolve in a diluent without disrupting the association between the silver cation and the citrate anion; nor has it been shown that reconstituted solutions have antimicrobial properties.

The invention provides reconstituted silver dihydrogen citrate and citric acid compositions containing from about 0.05 ppm to about 10,000 ppm of silver ion ($Ag^+$). An effective concentration of silver dihydrogen citrate depends on the microbe against which protection is sought, the substrate to be treated and the existing or potential bioburden on the substrate, and presence or absence of additional antimicrobial actives in the diluent. In some embodiments, an antimicrobially effective concentration of silver ion ranges from about 0.075 ppm to about 2,500 ppm, especially about 0.1 to about 1,000 ppm.

Thus, the invention provides a method of using an anhydrous silver dihydrogen citrate composition produce a reconstituted silver dihydrogen citrate solution. The method comprises combining the anhydrous composition with a diluent. The diluent is a solvent capable of dissolving the silver dihydrogen citrate and citric acid. In some embodiments, a suitable diluent is an aqueous solvent, such as water or a solution comprising water and an additional water-soluble ingredient For example the diluent can be water, ethanol or a combination of water and ethanol, such as a 10% solution of ethanol in water.

The invention further provides for reconstituting the anhydrous silver dihydrogen citrate and citric acid compositions with a diluent that is substantially pure water. The term "substantially pure water" means water that is essentially free of contaminants or antimicrobial agents, such as ethanol. Examples of substantially pure water are distilled water, double distilled water, double distilled deionized water, ultrafiltered water and water for injection.

The invention further provides for reconstituting the anhydrous silver dihydrogen citrate and citric acid compositions with tap water, with "fresh water," that is water obtained from rivers, lakes, streams, reservoirs, etc., and with "treated water," that is effluent water that has been treated to remove contaminants. In most normal circumstances, normal tap water will suffice as a diluent, although a purer form of water may be used if necessary.

The invention also provides for reconstituting the anhydrous silver dihydrogen citrate and citric acid compositions with a diluent that is an aqueous solution comprising water and another ingredient. The other ingredient can be a cleaning agent, an antibacterial agent or another type of ingredient. Exemplary cleaning agents include detergents. Exemplary antimicrobials include ethanol. The invention provides diluents comprising water and a member of the group consisting of detergents, alcohols and combinations thereof. Exemplary diluents include aqueous ethanol, aqueous sodium dodecyl sulfate, and aqueous mixtures of ethanol and sodium dodecyl sulfate. For example, the invention provides as a diluent an aqueous solution of about 0.1 to about 10% ethanol and optionally about 0.0001 to about 0.1% detergent. An exemplary diluent comprises about 2% ethanol and greater than about 0.01% detergent in water.

The combination of silver dihydrogen citrate and ethanol produces unexpected synergistic disinfectant and anti-microbial properties. As compared to an aqueous ethanol composition without silver dihydrogen citrate, the invention provides disinfectant and antimicrobial effects at a lower concentration of alcohol than is necessary without the silver dihydrogen citrate.

The invention further provides methods of using anhydrous silver dihydrogen citrate compositions to produce an antimicrobial effect. The methods include combining an anhydrous silver dihydrogen citrate composition with a diluent to produce a reconstituted silver dihydrogen citrate solution. The methods further comprise applying the reconstituted silver dihydrogen citrate and citric acid solution to a substrate. The term "substrate" is generically used herein to mean any surface, article or environment that is in need of antimicrobial treatment.

Various surfaces may be treated with compositions comprising silver dihydrogen citrate, including countertops, floors, glass surfaces, metal surfaces (such as stainless steel, chrome and copper surfaces), tile surfaces, concrete surfaces, vinyl flooring and painted surfaces. The term "surface" is used herein to connote any surface, including interior and exterior surfaces of various objects, including interiors of containers (such as boilers, water tanks, swimming pools, etc.), interiors of pipes, exteriors of household fixtures and appliances, countertops, glass windows and doors. The term "surface" is used herein to distinguish over a whole article. The reconstituted silver dihydrogen citrate and citric acid solutions are applied to the surface by in a conventional manner, such as by pouring, spraying or swabbing the solution onto the surface. The solution are conveniently wiped or rinsed off the surface, or are advantageously left on the surface to dry, thereby providing a long-lasting antimicrobial residue or film on the surface.

The invention further includes methods of treating various articles, such as fabrics, metal articles, plastic articles, natural products and other articles that are often treated with aqueous cleaning solutions. For example, the invention provides for treating food items with a reconstituted silver dihydrogen citrate and citric acid composition. Exemplary food items that are treated in such a manner include vegetables and fruits. Exemplary vegetables that may be treated in this manner include: roots (such as carrots, beets, radishes); tubers (such as potatoes, turnips, sweet potatoes and yams); bulbs (such as onions, scallions); corms (such as garlic); green leafy vegetables (such as spinach, kale, lettuce and cabbage); cruciferous sprouts (such as broccoli and cauliflower); and legumes (such as beans and peanuts). Exemplary fruits that may be treated in this manner include: squash, melons, apples, peaches, pears, bananas, tomatoes, citrus (such as oranges, grapefruit, tangerines, tangelos, lemons and limes), grapes and olives. The invention provides for spraying or wiping the silver dihydrogen citrate composition onto the food item. The invention alternatively provides for dipping the food item into a the solution.

The invention also embraces methods of treating a variety of articles with reconstituted silver dihydrogen citrate solutions. For example, the solutions may be sprayed or wiped onto a variety of items including mechanical parts used in food service or food process manufacturing. The solutions may also be used to clean toys and other items handled by children and infants. The solutions may further be used to clean fabric items, such as clothing, wash rags, bedding and other fabric items. The invention provides reconstituted silver dihydrogen citrate compositions as soaking compositions for disinfecting cooking utensils, eating utensils and cutlery.

The invention further includes antimicrobially effective silver dihydrogen citrate compositions. The term "antimicrobially effective" means that the composition is effective to halt or reduce the spread of one or more microbes, prevent infestation by one or more microbes, kill one or more microbes, or a combination of these effects. The term microbe includes a bacterium, virus or fungus. Aqueous silver dihydrogen citrate compositions have been shown to be effective against a variety of indicator and pathogenic microbes, including bacteria, such as: *Pseudomonas aeruginosa, Salmonella choleraesuis, Staphylococcus aureus, Proprionibacterium acnes, Escherichia coli, Listerid monocytogenes* and *Enterococcus faecium;* viruses such as: Human immunodeficiency virus 1 (HIV 1), Herpes simplex virus 2 (HSV 2), Influenza A, Rhinovirus and Poliovirus type 2; and fungi such as *Trichophyton mentagrophytes*.

The invention may be more fully appreciated with reference to the following illustrative and non-limiting examples. Other embodiments of the invention may be practiced within the scope of the present invention.

EXAMPLES

Example 1

Preparation of Stock Silver Dihydrogen Citrate Solution

Water was introduced into a reverse osmosis unit, passing through a semi-permeable membrane to remove impurities and producing deionized water. Anhydrous 99% pure citric acid was mixed with the water to produce 200 gallons of a 20% (wt/vol) (796 g citric acid per gallon water) solution. The 200 gallons of 20% citric acid were directed into an ion chamber containing having positive and negative electrodes, each consisting of 200 troy ounces of 999 fine silver. The positive and negative electrodes were spaced at least 2.0 mm apart, allowing the citric acid solution to pass between the two electrodes. An ion generation controller (IGC) power supply including a positive and a negative conductor was attached to the positive and negative electrodes. The IGC applied a current of 5 amps at 17 volts, pulsed every 9 seconds, with a polarity change at 1 minute intervals. Throughout the process, the electrode gap was adjusted in order to maintain the 5 amp-17 volt output. The electric current flow caused an ion current to flow between the positive and negative electrodes, producing free silver ions within the diluted citric acid solution. The silver ions reacted with the citric acid in the citric acid solution to produce the silver dihydrogen citrate solution. The 20% citric acid solution was recirculated through the ion chamber at 50 gallons per minute for 144 hours until the desired silver ion concentration was obtained. The silver dihydrogen citrate solution was then allowed to sit in order to allow any solids formed during the procedure to precipitate. The resulting product was a silver dihydrogen citrate solution having a silver ion concentration of 2400 ppm. Hereafter, this solution is referred to as a stock solution. The stock solution can be used immediately per the following examples or stored for later use.

It should be understood by those skilled in the art that numerous variations in the size and/or spacing of the electrodes and numerous variations in the peak voltage and numerous variations in the timing sequence of the intermittent voltage polarity can readily be used to obtain the silver dihydrogen citrate for use in the invention.

Example 2

Preparation of Anhydrous Silver Dihydrogen Citrate

A 1,000 ml sample of the stock solution, prepared as in foregoing Example 1, was obtained from SSA Batch No. 04.06.03 and was confirmed to have a concentration of ionic silver of 2400 ppm using an Orion™ 290A processor with an ion specific electrode (ISE). The processor was calibrated using Orion™ standard solutions.

The 1,000 ml stock solution was decanted into two 2.5"×8"×15" Pyrex™ heat resistant glass trays. The liquid stock solution level was approximately 1.5" in each tray.

The trays were then placed into a small commercial-grade freeze-drying unit, which consisted of a drying chamber with temperature control shelves, a condenser to trap water removed from the product, a cooling system to supply refrigerant to the temperature control shelves and condenser, a vacuum system to reduce the pressure in the chamber and condenser to facilitate the drying process. Cooling and vacuum pressure settings were kept within the standard ranges associated with freeze-drying aqueous solutions>50% water matrix.

After 99% of the water was removed from the product, the large, coarse crystals were collected from the trays and ground into a fine crystalline powder, weighed and stored at an ambient room temperature (74° F.) for one week. Total crystal weight was 206.12 g.

Example 3

Reconstitution of Silver Dihydrogen Citrate Solution

The crystalline powder from Example 2 was then reconstituted using approximately 794 ml of pharmaceutical-grade pure water in a 1,000 ml Pyrex glass flask. The solution was then agitated via magnetic stirrer for 30 minutes and put into a light-proof storage cabinet for 24 hours.

The concentration of silver ion in the reconstituted solution was then measured using the Orion 290A processor and ISE described in Example 2. Measurements were obtained at 24, 28 and 72 hours and at intervals of 1 week for a total of 4 weeks. The 24 hour reading and the week 4 readings were 2398 ppm and 2407 ppm, respectively. These concentrations are essentially the same as the 2400 ppm stock solution (within the % error operational specifications for the Orion 290A™ processor).

Example 4

Antimicrobial Efficacy of Reconstituted Silver Dihydrogen Citrate Solutions

In order to demonstrate the efficacy of silver dihydrogen citrate compositions as preservatives, stock solutions of silver dihydrogen citrate, as described in Example 1, were subjected to Preservative Challenge Tests. The Preservative Challenge Tests were performed according to the European Pharmacopoeia test method 4.04/5.01.03.00 for Category 2 products (topically used products made with aqueous bases or vehicles, nonsterile nasal products, emulsions including those applied to mucous membranes.

Bacterial test organisms and yeasts were cultivated on Casein Soymeal peptone agar and fungal test organisms on Sabouraud 4% glucose agar for 18-24 hours at 35° C. (bacteria), 48 hours at 25° C. (*Candida*) or 1 week at 25° C. (*Aspergillus*).

After incubation, the bacterial and yeasts were harvested by washing off the surface of the agar plates with 0.9% sodium chloride. *Aspergillus* was harvested by washing off the agar plate surface with 0.9% sodium chloride/0.01% Tween 80.

The suspension of test microorganisms were diluted with 0.9% sodium chloride to the final test organism suspensions with a density of ~$10^8$ colony forming units.

Per test organisms, 20 g of the test product were weight in glass jars (250 ml jars with screw cups from Schott/Germany) and contaminated with 0.2 ml of the test organism suspension. The microorganisms were carefully distributed in the test product by stirring with a glass spatula.

The so contaminated test products were stored at 20-25° C. in the dark.

Samples of 1 g material were taken immediately after contamination of the test products and 2 days, 7 days, 14 days and 28 days after contamination.

The samples were diluted in 0.9% sodium chloride and 0.1 ml aliquots of the dilutions were spread on agar plates by means of Drigalsky spatula. An adequate inactivator (neutralizer) of the specific antimicrobial was incorporated in the diluent used for preparation of the product dilutions and in the agar plates used for assessment of the total number of viable cells.

The agar plates were incubated for 24 hours at 35° C. (bacteria and yeasts) or 3 days at 25° C. (*Aspergillus*) and the grown colonies were counted after the incubation phase. The colonies were counted and the number of viable cells (colony forming units) per g test product was calculated. The log reduction of the microorganisms in the product was then calculated (see tables with results of Preservation Challenge Tests below).

Test Strains:

*Pseudomonas aeruginosa* ATCC 9027; NCIMB 8626; CIP 82.118

*Staphylococcus aureus* ATCC 6538; NCTC 10788; NCIMB 9158; CIP 4.83

*Candida Albicans* ATCC 10231; NCPF 3179; IP 48.72

*Aspergillus niger* ATCC 16404; IMI 149007; IP 1431.83

Silver dihydrogen citrate was tested in a variety of formulations for its antimicrobial effects. The following Tables 1-3 show the results of these tests:

TABLE 1

Preservative Challenge Test/Deodorant Emulsion

| Test organisms | Staph. Aureus | E. coli | Ps. Aeruginosa | C. albicans | A. niger |
|---|---|---|---|---|---|
| O/W PK03-260-01 (Placebo) | | | | | |
| 2 days after contamination | <100 | <100 | <100 | 6.0 × 10E4 | 1.8 × 10E5 |
| 7 days after contamination | <100 | <100 | <100 | 1.6 × 10E4 | 3.0 × 10E5 |
| 14 days after contamination | <100 | <100 | <100 | 8.8 × 10E3 | 2.8 × 10E5 |
| 28 days after contamination | <100 | <100 | <100 | 1.4 × 10E3 | n.d |
| O/W PK03-260-01 (0.1% Axenohl | | | | | |
| 2 days after contamination | <100 | <100 | <100 | <100 | 1.6 × 10E5 |
| 7 days after contamination | <100 | <100 | <100 | <100 | 2.6 × 10E5 |
| 14 days after contamination | <100 | <100 | <100 | <100 | 1.2 × 10E5 |
| 28 days after contamination | <100 | <100 | <100 | <100 | n.d |
| O/W PK03-260-01 (0.3% Axenohl) | | | | | |
| 2 days after contamination | <100 | <100 | <100 | <100 | 1.4 × 10E5 |
| 7 days after contamination | <100 | <100 | <100 | <100 | 1.2 × 10E5 |
| 14 days after contamination | <100 | <100 | <100 | <100 | 1.0 × 10E5 |
| 28 days after contamination | <100 | <100 | <100 | <100 | n.d |

TABLE 2

Preservative Challenge Test/Deodorant Emulsion

| Test organisms | Staph. Aureus | E. coil | Ps. Aeruginosa | C. albicans | A. niger |
|---|---|---|---|---|---|
| O/W PK03-260-01 (Placebo) | | | | | |
| 2 days after contamination | $2.0 \times 10E4$ | $1.0 \times 10E6$ | $1.0 \times 10E6$ | $1.0 \times 10E6$ | $2.0 \times 10E5$ |
| 7 days after contamination | <100 | $3.1 \times 10E3$ | $4.4 \times 105$ | $6.2 \times 10E5$ | $3.0 \times 10E5$ |
| 14 days after contamination | <100 | $1.0 \times 10E2$ | $1.1 \times 10E6$ | $1.3 \times 10E6$ | $3.5 \times 10E5$ |
| 28 days after contamination | <100 | $1.2 \times 10E2$ | $6.0 \times 10E7$ | $1.1 \times 10E6$ | n.d |
| O/W PK03-260-01 (0.1% Axenohl) | | | | | |
| 2 days after contamination | $5.0 \times 10E2$ | $4.0 \times 10E2$ | $3.0 \times 10E2$ | $4.0 \times 10E3$ | $1.4 \times 10E5$ |
| 7 days after contamination | <100 | $2.0 \times 10E2$ | <100 | $3.4 \times 10E4$ | $1.8 \times 10E5$ |
| 14 days after contamination | <100 | <100 | <100 | $1.1 \times 10E5$ | $2.0 \times 10E5$ |
| 28 days after contamination | <100 | <100 | <100 | $4.0 \times 10E5$ | n.d |
| O/W PK03-260-01 (0.3% Axenohl) | | | | | |
| 2 days after contamination | $3.0 \times 10E2$ | $4.0 \times 10E3$ | $7.0 \times 10E2$ | $4.0 \times 10E3$ | $1.8 \times 10E5$ |
| 7 days after contamination | <100 | $2.0 \times 10E2$ | <100 | $2.4 \times 10E3$ | $2.4 \times 10E5$ |
| 14 days after contamination | <100 | <100 | <100 | $1.2 \times 10E3$ | $2.4 \times 10E5$ |
| 28 days after contamination | <100 | <100 | <100 | $2.0 \times 10E2$ | n.d |
| 28 days after contamination | | | | | |

TABLE 3

Preservative Challenge Test/Shower Gel

| Test organisms | Staph. Aureus | E. coli | Ps. Aeruginosa | C. albicans | A. niger |
|---|---|---|---|---|---|
| FB02-060-03 (Placebo) | | | | | |
| 2 days after contamination | $4.0 \times 10E2$ | $2.2 \times 10E5$ | in progress | $2.2 \times 10E5$ | $2.4 \times 10E5$ |
| 7 days after contamination | <100 | $1.1 \times 10E5$ | in progress | $2.1 \times 10E5$ | $3.6 \times 10E5$ |
| 14 days after contamination | <100 | $8.2 \times 10E4$ | in progress | $9.0 \times 10E4$ | $3.6 \times 10E5$ |
| 28 days after contamination | n.d | n.d | in progress | n.d | n.d |
| Body Shampoo (0.1% Axenohl) | | | | | |
| 2 days after contamination | <100 | $1.8 \times 10E4$ | <100 | <100 | $2.0 \times 10E5$ |
| 7 days after contamination | <100 | <100 | <100 | <100 | $3.0 \times 10E5$ |
| 14 days after contamination | <100 | <100 | <100 | <100 | $3.2 \times 10E5$ |
| 28 days after contamination | <100 | <100 | <100 | <100 | n.d |
| Body Shampoo (0.3% Axenohl) | | | | | |
| 2 days after contamination | <100 | $6.0 \times 10E3$ | <100 | <100 | $1.8 \times 10E5$ |
| 7 days after contamination | <100 | <100 | <100 | <100 | $2.4 \times 10E5$ |
| 14 days after contamination | <100 | <100 | <100 | <100 | $2.4 \times 10E5$ |
| 28 days after contamination | <100 | <100 | <100 | <100 | n.d |
| 28 days after contamination | | | | | |

The invention may be more fully appreciated with reference to the following illustrative and non-limiting examples. Other embodiments of the invention may be practiced within the scope of the invention.

What is claimed is:

1. An anhydrous composition comprising silver dihydrogen citrate and citric acid prepared by removing water from an aqueous stock solution comprising an antimicrobial amount of silver dihydrogen citrate and citric acid, wherein, when said composition is reconstituted by diluting in water, a stable aqueous solution containing an antimicrobial amount of silver dihydrogen citrate substantially equivalent to that present in said stock solution is obtained.

2. The composition of claim 1, which contains less than about 0.5% water.

3. The composition of claim 1, which is crystalline.

4. The composition of claim 1, wherein the composition comprises a molar excess of citric acid over silver dihydrogen citrate.

5. The composition of claim 4, wherein the composition comprises at least a 5 fold molar excess of citric acid over silver dihydrogen citrate.

6. A process to make the anhydrous composition of claim 1 comprising silver dihydrogen citrate and citric acid, comprising the steps of:
   (a) providing a stock solution comprising silver dihydrogen citrate, citric acid and water;
   (b) freezing the stock solution to form a frozen solution; and
   (c) freeze-drying the frozen solution to form the anhydrous composition.

7. The process of claim 6, wherein the citric acid is a molar excess of citric acid over silver dihydrogen citrate.

8. The process of claim 6, wherein step (c) further comprises heating the frozen solutions.

9. A method to prepare a stable aqueous solution containing an antimicrobial amount of silver dihydrogen citrate which method comprises diluting the composition of claim 1 with an aqueous diluent.

10. The method of claim 9, wherein the aqueous diluent is substantially pure water.

11. The method of claim 9, wherein the aqueous diluent comprises water and one or more alcohols, one or more detergents, or both.

12. A method to disinfect a substrate which method comprises applying the antimicrobial aqueous solution prepared by the method of claim 9 to a substrate, whereby an antimicrobial effect is achieved.

13. The method of claim 12, wherein the substrate is a solid surface, a food article or a non-food article.

14. The method of claim 13, wherein the solid surface is the interior of a pipe, a holding tank, a swimming pool, a spa, a cooling system or a cooling tower.

15. The method of claim 12 wherein the antimicrobial effect is biocidal or biofilm control.

16. The method of claim 12, wherein the antimicrobial effect is food preservation.

17. The composition of claim 5, wherein the composition comprises at least a 15 fold molar excess of citric acid over silver dihydrogen citrate.

18. The composition of claim 1, wherein the aqueous stock solution consists essentially of 20% wt/vol of citric acid and 2,400 ppm silver ion.

* * * * *